US008450297B2

(12) United States Patent
Rosenberg et al.

(10) Patent No.: US 8,450,297 B2
(45) Date of Patent: May 28, 2013

(54) RAPID TWO-STEP SYNTHESIS OF ANTI-COAGULANTS

(75) Inventors: Robert D. Rosenberg, Cambridge, MA (US); Kuberan Balagurunathan, Salt Lake City, UT (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/204,391

(22) Filed: Aug. 16, 2005

(65) Prior Publication Data

US 2006/0111317 A1      May 25, 2006

Related U.S. Application Data

(63) Continuation of application No. 10/986,058, filed on Nov. 12, 2004, now Pat. No. 7,655,445.

(60) Provisional application No. 60/601,636, filed on Aug. 16, 2004.

(51) Int. Cl.
*A61K 31/727* (2006.01)
*C08B 37/00* (2006.01)
*C07H 5/04* (2006.01)
*C07H 5/06* (2006.01)

(52) U.S. Cl.
USPC .......................................................... 514/56

(58) Field of Classification Search
None
See application file for complete search history.

(56) References Cited

U.S. PATENT DOCUMENTS

| | | | |
|---|---|---|---|
| 4,756,884 | A | 7/1988 | Hillman et al. |
| 4,861,712 | A | 8/1989 | Bartl et al. |
| 4,946,775 | A | 8/1990 | Yin |
| 5,037,810 | A | 8/1991 | Saliba et al. |
| 5,059,525 | A | 10/1991 | Bartl et al. |
| 5,110,727 | A | 5/1992 | Oberhardt |
| 5,290,695 | A | 3/1994 | Morikawa |
| 5,300,779 | A | 4/1994 | Hillman et al. |
| 5,362,641 | A | 11/1994 | Fuks et al. |
| 5,908,837 | A | 6/1999 | Cohen et al. |
| 2002/0062019 | A1 | 5/2002 | Oreste |
| 2003/0023079 | A1 | 1/2003 | Oreste |

FOREIGN PATENT DOCUMENTS

WO    WO 01/02597    1/2001

OTHER PUBLICATIONS

Nader et al. Glycoconjugate Journal 16, 265-270 (1999).*
Toida et al. The Journal of Biological Chemistry, vol. 271, No. 50, Issue of Dec. 13, pp. 32040-32047, 1996.*
Kuberan, The Journal of Biological Chemistry, vol. 278, No. 52, Dec. 26, pp. 52613-52621, 2003.*
Casu et al. Carbohydrate Letters, vol. 1, pp. 107-114.*
R.D. Rosenberg, P. S. Damus, J Biol Chem 248, 6490-505 (Sep. 25, 1973).
R. D. Rosenberg, N. W. Shworak, J. Liu, J. J. Schwartz, L. J. Zhang, Journal of Clinical Investigation 99, 2062-2070 (May 1, 1997).
Z. L. Wu, L. Zhang, D. L. Beeler, B. Kuberan, R. D. Rosenberg, Faseb J 16, 539-45 (Apr. 2002).
B. Kuberan et al., Journal of the American Chemical Society 124, 8707-8718 (Jul. 24, 2002).
M. Manzoni et al. Journal Bioactive Compatible Polymers, 1996, 11, 301-311.
Johansson et al, Biotechnol. Lett., 8 (1986) 421-424.
W. F. Vann, et al "The structure of the capsular polysaccharide (K5 antigen) of urinary-tract-infective *Escherichia coli* O10:K5:H4. A polymer similar to desulfo-heparin." K. Jann, Eur J Biochem 116, 359-64 (1981).
Orellana, C. B., et al "Molecular cloning and expression of a glycosaminoglycan N-acetylglucosaminyl N-deacetylase/N-sulfotransferase from a heparin-producing cell line." J Biol Chem 269, 2270-6 (1994).
J. Li et al., "Biosynthesis of heparin/heparan sulfate. cDNA cloning and expression of D-glucuronyl C5-epimerase from bovine lung." J Biol Chem 272, 28158-63 (1997).
H. Habuchi et al., "The occurrence of three isoforms of heparan sulfate 6-O-sulfotransferase having different specificities for hexuronic acid adjacent to the targeted N-sulfoglucosamine."J Biol Chem 275, 2859-68 (2000).
J. Liu, et al."Purification of heparan sulfate D-glucosaminyl 3-O-sulfotransferase." Journal of Biological Chemistry 271, 27072-27082 (1996).
N. W. Shworak et al., "Multiple isoforms of heparan sulfate D-glucosaminyl 3-O-sulfotransferase. Isolation, characterization, and expression of human cdnas and identification of distinct genomic loci." Journal of Biological Chemistry 274, 5170-5184 (1999).
P. Sinay et al. Carbohydrate Research 132, C5-C9 (1984).
M. Petitou et al., Nature 398, 417-422 (Apr. 1, 1999).
S.E. Stringer, J.T. Gallagher, Journal Biology Chemistry 272, 20508-14 (Aug. 15, 1997).

* cited by examiner

*Primary Examiner* — Layla Bland
(74) *Attorney, Agent, or Firm* — Mark S. Cohen; Pearl Cohen Zedek Latzer, LLP

(57) ABSTRACT

The present invention provides methods for the production of N-deacetylate N-sulfate derivatives of non-sulfated N-acetyl heparosan (HS) polysaccharides, compounds thus obtained and compositions comprising same. This invention also provides applications of N-deacetylate N-sulfate derivatives of non-sulfated N-acetyl heparosan (HS) polysaccharides, and compositions comprising same, for use in controlling coagulation and treating thrombosis.

7 Claims, 4 Drawing Sheets

RAPID TWO-STEP SYNTHESIS OF ANTI-COAGULANTS

CROSS-REFERENCE TO RELATED APPLICATIONS

This application is a continuation of U.S. application Ser. No. 10/986,058, filed on Nov. 12, 2004, now U.S. Pat. No. 7,655,445, which claims the benefit of U.S. Provisional Application No. 60/601,636, filed on Aug. 16, 2004, and are hereby incorporated by reference in their entirety.

GOVERNMENT INTEREST STATEMENT

This invention was made in whole or in part with government support under grant numbers HL63609 and HL66105, awarded by the National Institute of Health. The government may have certain rights in the invention.

FIELD OF THE INVENTION

This invention provides Heparin derived anti-coagulants and methods for synthesizing Heparin-derived anticoagulants. Further, this invention provides methods for a rapid two-step synthesis process for heparin-derived anticoagulants, having diminished PF4 binding capacity, and methods of use thereof.

BACKGROUND OF THE INVENTION

Heparin, a strongly acidic, linear sulfated polysaccharide anti-coagulant, is used in the prevention and treatment of thrombosis. Heparin was first isolated from the liver from which it derives its name (1). Heparin-like polysaccharides are shown to interact with numerous proteins and orchestrate many different biologic functions (2). A unique penta-saccharide domain present within heparin was found to bind to Antithrombin III (ATIII) in a highly specific manner to induce a conformational change that is sufficient to promote rapid inhibition of blood coagulation (3, 4). Sinay and coworkers pioneered the original chemical synthesis of the ATIII binding pentasaccharide and analogs (5, 6).

Heparin-induced thrombocytopenia (HIT) is an immunologic disorder associated with heparin treatment (7). HIT paradoxically increases thrombosis, which occurs in about 30% of the recognized HIT cases, and is a major cause of morbidity and mortality in patients treated with heparin. It has been shown that HIT is induced by antibodies directed against a PF4-heparin complex. The complex formation requires a 2-O sulfated iduronic acid residue (8). Engineering new heparin-like anticoagulants that are unable to form heparin-PF4 complexes, would be a major advance in anticoagulation therapy. There is also an increased concern for the potential spread of diseases of animal origin to humans, such as bovine encephalopathy, due to the use of animal derived heparin. The above-mentioned potential side effects of animal derived heparin prompted the chemical synthesis of heparin-based anticoagulants. Despite many advances made in chemical synthesis, this approach is cumbersome and time consuming.

SUMMARY OF THE INVENTION

This invention provides, in one embodiment, Heparin-derived anticoagulants and methods for the production of a polysaccharide molecule, a compound or a composition comprising N-deacetylate N-sulfate derivatives of non-sulfated N-acetyl heparosan (HS) polysaccharides. This invention also provides, in another embodiment, methods of use of N-deacetylate N-sulfate derivatives of non-sulfated N-acetyl heparosan (HS) polysaccharides, and compositions comprising same, for use in controlling coagulation and treating thrombosis.

In one embodiment, the invention provides N-deacetylate N-sulfate derivatives of non-sulfated N-acetyl heparosan (HS) polysaccharide. In one embodiment, the invention provides a compound, represented by the structure of Formula I.

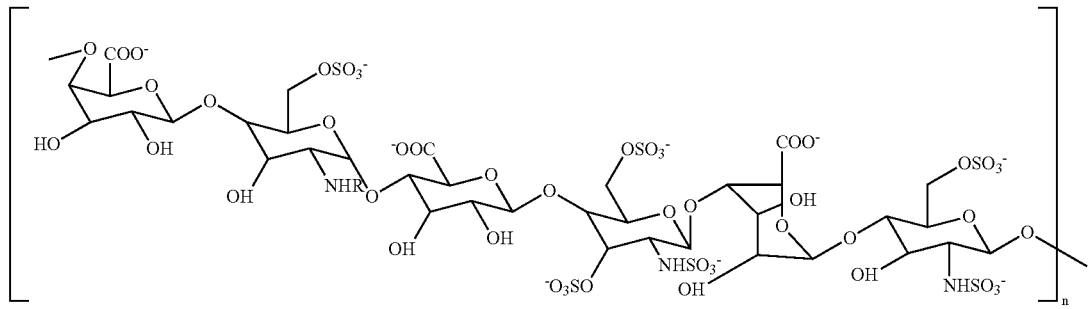

In one embodiment, R is an acetyl group. In another embodiment, R is a sulfonate group.

In another embodiment the invention provides compositions comprising N-deacetylate N-sulfate derivatives of non-sulfated N-acetyl heparosan (HS) polysaccharide, represented by the structure of Formula I.

The invention provides, in another embodiment, a method for the preparation of non-sulfated N-acetyl heparosan (HS) polysaccharide derivatives represented by Formula I, comprising the steps of: (a) contacting a non-sulfated N-acetyl heparosan (HS) polysaccharide with N-deacetylase-N-sulfotransferase and glucuronosyl C-5 epimerase to generate an iduronic acid-enriched polysaccharide; (b) contacting the product of step (a) with 6-O sulfotransferase (6-OST) and 3-O sulfotransferase (3-OST); and (c) isolating the product of step (b), thereby yielding N-deacetylate N-sulfate derivatives of non-sulfated N-acetyl heparosan.

In another embodiment, the invention provides a method for the preparation of novel glycosaminoglycans, comprising the steps of: (a) contacting a non-sulfated N-acetyl heparosan (HS) polysaccharide with the enzymes N-deacetylase-N-sulfotransferase and glucuronosyl C-5 epimerase to generate an iduronic acid-enriched polysaccharide; (b) contacting the product of step (a) with the enzymes 6-O sulfotransferase (6-OST) and 3-O sulfotransferase (3-OST); and (c) isolating the product of step (b), thereby yielding N-deacetylate N-sulfate derivatives of non-sulfated N-acetyl heparosan.

In another embodiment, the invention provides a method for preventing or treating thrombosis in a subject, comprising providing said subject with an effective amount of a compound or composition comprising N-deacetylate N-sulfate derivatives of non-sulfated N-acetyl heparosan (HS) polysaccharide, represented by the structure of Formula I.

DETAILED DESCRIPTION OF THE INVENTION

Figure 1:
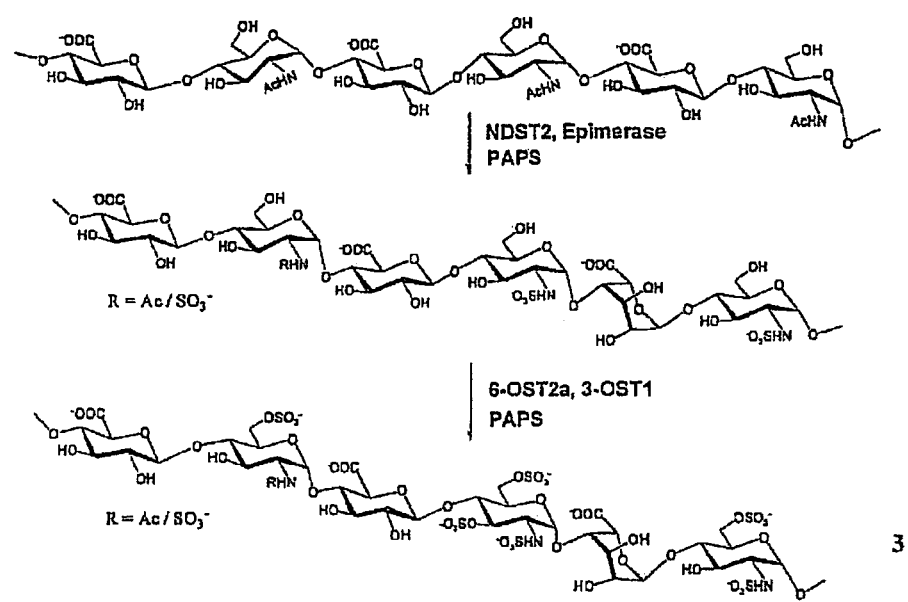
FIG. 1 schematically depicts the enzymatic synthesis of N-deacetylate N-sulfate derivatives of non-sulfated N-acetyl heparosan (HS) polysaccharides.

In one embodiment, the invention provides for a compound comprising an N-deacetylate N-sulfate derivative of non-sulfated N-acetyl heparosan (HS) polysaccharide, represented by the structure of Formula I.

As used herein, the terms "compound of Formula I" or "compound represented by the structure of Formula I" are synonymous, and refer to N-deacetylate N-sulfate derivatives of non-sulfated N-acetyl heparosan (HS) polysaccharide, represented by the structure of the following formula:

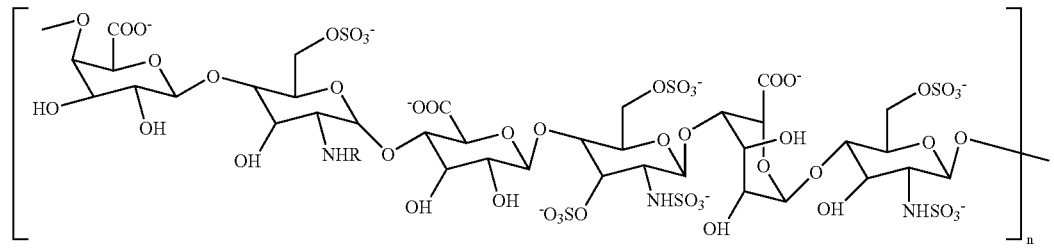

wherein R is an acetyl or sulfonate group, and n is an integer.

In one embodiment, the compound of Formula I has an acetyl group (Ac) at each position indicated by an R in the formula hereinabove. In another embodiment, the compound has a sulfonate group ($SO_3^-$) at each position indicated by an R in the formula hereinabove. In another embodiment, the compound has a Hydrogen (H) at each position indicated by an R in the formula hereinabove. In another embodiment, the compound has mixed substitutions of Ac $SO_3^-$ or H groups at positions indicated by an R in the formula hereinabove. It is to be understood that any substitutions of formula I achieved via the methods described herein, with anti-coagulant activity are to be considered as part of this invention. Such compounds may have additional therapeutic activity, as well, including antiviral activity.

In another embodiment, n is an integer with a value of 50-250. In one embodiment, n is an integer with a value of 1-1,000, or, in another embodiment, 1-100, or in another embodiment, 1-50, or in another embodiment, 1-25, or in another embodiment, 1-15. In another embodiment, n is an integer with a value of 100-1,000,000. In another embodiment, n is an integer with a value of 100-100,000. In another embodiment, n is an integer with a value of 100-1,000. In another embodiment, n is an integer with a value of 1,000-1,000,000, or in another embodiment, 1,000-100,000 or in another embodiment, 1,000-50,000, or in another embodiment, 1,000-25,000, or in another embodiment, 1,000-10,000.

It is to be understood that reference to "the compound of Formula I" is meant to include any molecule, with a sufficient percentage of atoms identical with that represented by the structure of Formula I. The compound may, in one embodiment, exhibit less molecular identity in terms of atomic correspondence yet exhibit functional homology, for example, in terms of the sulfonation, or the absence of sulfonation at key positions. The term "homology" or "correspondence", as used herein, is meant to represent identity, as indicated, or comparability, indicating an ability to conform structurally or/thereby perform functionally. Thus any molecule synthesized via the methods described herein, wherein the product exhibits molecular identity, or structural homology, and/or possesses anti-coagulant activity, is to be considered as part of this invention.

Homology and/or comparability may be determined by methods well described in the art, including immunoblot analysis, HPLC, Mass Spectroscopy, functional assays disclosed herein, demonstrating anti-coagulant activity and others well known to those skilled in the art.

The term "derivative" as used herein, is meant to encompass any molecule that is a product of the manipulation of an index compound, via any of the steps comprising the rapid 2-step synthesis method disclosed herein. A derivative of non-sulfated N-acetyl heparosan (HS) polysaccharide, therefore, indicates that the index compound, in this case the N-acetyl heparosan (HS) polysaccharide, is a starting material, and following the rapid 2-step synthesis outlined herein, the product is referred to as a derivative of non-sulfated N-acetyl heparosan (HS) polysaccharide.

In one embodiment, the derivative will, following the rapid 2-step synthesis outlined herein, produce a compound represented by the structure of Formula I.

Figure 4:
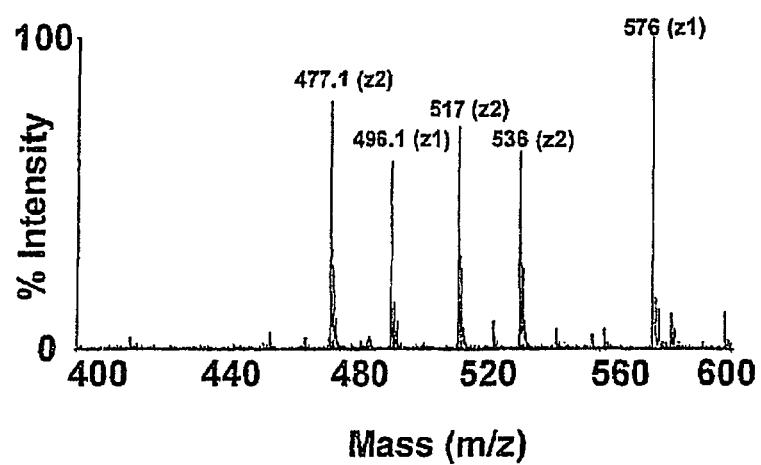
FIG. 4 demonstrates the results of a mass spectrometric analysis of N-deacetylate N-sulfate derivatives of non-sulfated N-acetyl heparosan (HS) polysaccharides.

In one embodiment, the N-deacetylate N-sulfate derivatives of non-sulfated N-acetyl heparosan (HS) polysaccharide exhibit a mass spectrum comparable to that of FIG. 4.

In another embodiment, the compound comprising N-deacetylate N-sulfate derivatives of non-sulfated N-acetyl heparosan (HS) polysaccharide represented by Formula I comprises at least 1 tri-sulfated disaccharide. The tri-sulfated disaccharide may, in one embodiment, contain a 3-O sulfated glucosamine unit, and as such represents another embodiment of the invention. The 3-O sulfated glucosamine unit may, in one embodiment, correspond to ? U-GlcNS3S6S.

In another embodiment, the compound of Formula I, following enzymatic cleavage with heparitinases, is characterized by the presence of a peak at m/z 576.0 [M-1H]-1, by mass spectroscopy.

Figure 2:
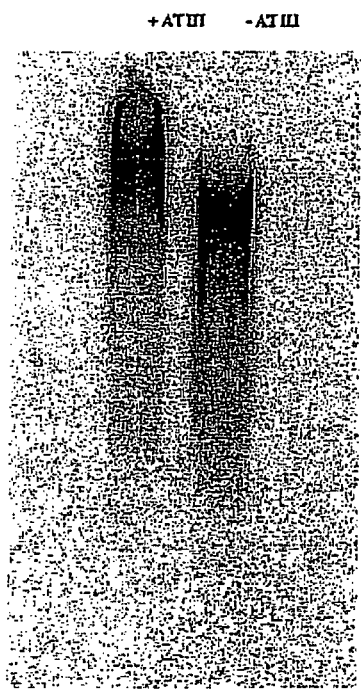
FIG. 2 demonstrates the results of a gel shift analysis of a N-deacetylate N-sulfate derivatives of non-sulfated N-acetyl heparosan (HS) polysaccharides (product 3, in the scheme in FIG. 1). PAP$^{35}$S-radiolabeled N-deacetylate N-sulfate derivatives of non-sulfated N-acetyl heparosan (HS) polysaccharides (10,000 counts) was reacted with 5 mg ATIII. Complex formation was analyzed by non-denaturing gel electrophoresis (4% polyacrylamide). The mobility of radiolabeled N-deacetylate N-sulfate derivatives of non-sulfated N-acetyl heparosan (HS) polysaccharides was compared with and without ATIII.
Figure 3:
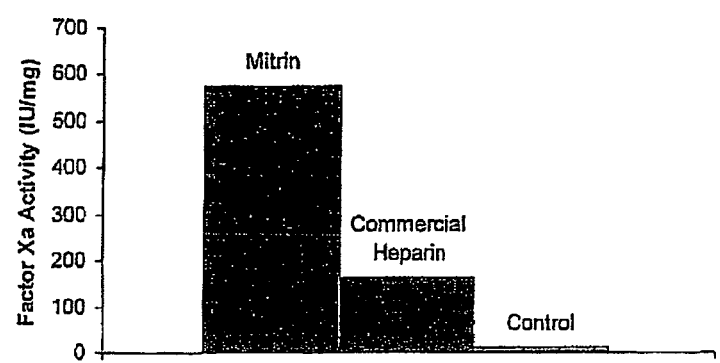
FIG. 3 demonstrates the biological activity of N-deacetylate N-sulfate derivatives of non-sulfated N-acetyl heparosan (HS) polysaccharides. Human factor Xa was incubated with antithrombin III in the presence of N-deacetylate N-sulfate derivatives of non-sulfated N-acetyl heparosan (HS) polysaccharides (polysaccharide 3), commercial heparin or polysaccharide 2 as a negative control. The percentage of inhibition of thrombin activity was calculated from three experiments performed in triplicate.

A compound comprising N-sulfate derivatives of N-acetyl heparosan (HS) polysaccharide represented by Formula I was demonstrated herein, via gel mobility shift assay, to bind to anti-thrombin III (ATIII) (FIG. 2). In comparison to commercial heparin, a greater percentage of the compound bound ATIII. Anticoagulant activity was further demonstrated via the heparin-dependent factor Xa inhibition assay [FIG. 3], where the specific activity of the compound represented by Formula I was approximately 4-5 times that of commercial heparin. LC/MS analysis [FIG. 4] demonstrated that the compound represented by Formula I contains multiple ATIII binding sites within the polymer, indicative of a greater ability to inhibit factor Xa. 2-O sulfated iduronic acid residues found in heparin, which are responsible for heparin binding to PF4, are absent in the compound represented by Formula I.

Coagulation is normally balanced by the fibrinolytic system, which helps to restore normal blood flow. Activation of the coagulation cascade is regulated by several systems of natural anticoagulant proteins. The term "anti-coagulant", as used herein, refers to any molecule that prevents the formation of a clot.

Anti-thrombin (AT) is known to neutralize the proteolytic activities of several clotting factors. Heparin exerts its anticoagulant effects by stimulating AT, which ultimately results in AT irreversible binding to and inhibition of coagulation factors. Heparin is also responsible for HIT, owing to its PF4 binding capacity. Anti-coagulants, which bind AT, or otherwise suppress coagulation, yet possess diminished PF4 binding capacity, or otherwise diminish the likelihood of HIT-phenomenon, are highly desirable.

Methods for measuring the effect on coagulation and/or the concentration in blood or plasma of direct or indirect inhibitors of activated coagulation factors include the assessment of inhibition of coagulation factors (e.g. FIIa and FXa) using chromogenic substrate analysis and so-called "clotting methods", e.g. the aPIT assay (activated partial thromboplastin time), the ACT assay (activated clotting time), the TT assay (thrombin time), the ECT assay (ecarin clotting time) and the Heptest® assay [see U.S. Pat. Nos. 4,946,775, 4,756,884, 4,861,712, 5,059,525, 5,110,727 and 5,300,779 and Thrombosis and Hemorrhage (op. cit.), and Kandrotas, R. J., Heparin Pharmokinetics and Pharmacodynamics, Clin. Pharmacokinet., vol. 22, 1992, pages 359-374].

Compounds represented by Formula I, in the present invention, will comprise, in one embodiment, at least 1 3-O sulfated tetrasaccharides within a polymer chain. The derivatives may comprise between 1-10 3-O sulfated tetrasaccharides within a 40-mer compound.

In another embodiment, compounds represented by Formula I comprise 3-O sulfated tetrasaccharides. In one embodiment, the 3-O sulfated tetrasaccharides correspond to: ? U-GlcNAc6S-GlcA-GlcNS3S6S. In another embodiment, the 3-O sulfated tetrasaccharides correspond to ? U-GlcNAc6S-GlcA-GlcNS3S. In another embodiment, the 3-O sulfated tetrasaccharides correspond to ? U-GlcNS6S-GlcA-GlcNS3S6S. In another embodiment, the 3-O sulfated tetrasaccharides are characterized by the presence of a peak at m/z 517.0 [M-2H]-2 by mass spectroscopy. In another embodiment, the 3-O sulfated tetrasaccharides are characterized by the presence of a peak at m/z 477.1 [4-2H]-2, by mass spectroscopy. In another embodiment, the 3-O sulfated tetrasaccharides are characterized by a peak at m/z 536.0 [M-2H]-2, by mass spectroscopy.

In another embodiment, the compound of Formula I is characterized by the presence of a peak at m/z 517.0 [N4-2H]-2, or 477.1 [M-2H]-2, or 536.0 [M-2H]-2, by mass spectroscopy. In another embodiment, N-deacetylate N-sulfate derivatives of non-sulfated N-acetyl heparosan (HS) polysaccharide, comprise any combination of the 3-O sulfated tetrasaccharides herein described.

In another embodiment, the invention provides compositions comprising the compound of Formula I. Such compositions and method of administration of same can vary based on the particular application, which is further discussed hereinbelow.

The compounds of the present invention, according to another aspect of the invention, can be synthesized via a rapid two-step enzymatic process, as exemplified herein. The NDST2 enzyme isoform was utilized to selectively N-deacetylate and N-sulfate glucosamine units of the N-acetyl heparosan (HS) polysaccharide. Deacetylation and N-sulfation was carried out in the presence of Heparan Sulfate C-5 epimerase, which generated the iduronic acid-enriched polysaccharide (Formula II). NDST2 and C5 epimerase activities were coupled in order to prepare, in a single step, N-sulfated polysaccharide (Formula H) containing both glucuronic and iduronic acid, without 2-O sulfation.

The final step in the synthesis was catalyzed by combined activity of 6-O sulfotransferase (6-OST) and 3-O sulfotransferase (3-OST). 6-O sulfation was coupled with 3-O sulfation, to produce the compound represented by the structure of Formula I. Coupling of 6-O sulfation and 3-O sulfation shortened the time required for total synthesis.

In one embodiment, there is provided a method for the preparation of N-sulfated N-deacetylated derivatives of non-sulfated N-acetyl heparosan (HS) polysaccharide derivatives represented by the structure of Formula I, comprising the steps of contacting a non-sulfated N-acetyl heparosan polysaccharide with the enzymes N-deacetylase-N-sulfotransferase and glucuronosyl C-5 epimerase to generate an iduronic acid-enriched polysaccharide; contacting the iduronic acid-enriched polysaccharide with the enzymes 6-O sulfotransferase (6-OST) and 3-O sulfotransferase (3-OST); and isolating the product, which yields an N-deacetylate N-sulfate derivative of non-sulfated N-acetyl heparosan corresponding to or homologous to Formula I.

In one embodiment, the glucuronosyl C-5 epimerase utilized for the synthesis may be a recombinant glucuronosyl C5 epimerase, a glucuronosyl C5 epimerase isolated from murine mastocytomas or a glucuronosyl C5 epimerase extracted from bovine liver.

In another embodiment, the N-deacetylase-N-sulfotransferase utilized for the synthesis may be a recombinant N-deacetylase-N-sulfotransferase. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells.

In another embodiment, the 6-O sulfotransferase utilized for the synthesis may be a recombinant enzyme. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells. In one embodiment, the 6-O sulfotransferase utilized may be the 6-OST1, 6-OST2 or 6-OST3 isoform. In another embodiment, 6-OST2 may be 6-OST2a or 6-OST2b.

In another embodiment, the 3-O sulfotransferase utilized for the synthesis may be a recombinant enzyme. The recombinant enzymes may be produced in insect cells, in yeast or in bacterial cells, via methods well known to one skilled in the art. In another embodiment, the enzymes may be isolated from any animal cell wherein the enzyme is naturally expressed, or from human cells. In one embodiment, the 3-O sulfotransferase utilized may be the 3-OST1 isoform, or in another embodiment, the 3-OST5 isoform, with resulting structures/tetrasaccharides considered as part of the present invention.

In one embodiment, the non-sulfated N-acetyl heparosan (HS) polysaccharide starting material is represented by the structure of Formula III.

According to this aspect of the invention, and in another embodiment, the Heparosan polysaccharide used as starting material may be a K5 polysaccharide, which may be obtained by fermentation of wild or cloned K5 producing *Escherichia coli* strains (See, for example, M. Manzoni et al. Journal Bioactive Compatible Polymers, 1996, 11, 301-311 or in WO 01/02597) Heparosan like polysaccharides may also be obtained from Pasturella multocida, as described (DeAngelis P L, et al., Carbohydrate Research. (2002) 337(17):1547-52). In another embodiment, the starting material may comprise Acharan Sulfate, and may be isolated from an African giant snail and utilized accordingly.

In another embodiment, the K5 starting materials may have a low molecular weight, with a distribution of from about 1,500 to about 15,000 Daltons (Da), or, in another embodiment, from about 2000 to about 9,000 Da with a mean molecular weight of about 5,000 Da, or, in another embodiment, a higher molecular weight, particularly with a distribution from about 10,000 to about 50,000 Da, or, in another embodiment, from about 20,000 to about 40,000 Da with a mean molecular weight of about 30,000 Da. In another embodiment, K5 has a molecular weight distribution from about 1,500 to about 50,000 Da, with a mean molecular weight of 20,000-25,000 Da.

In another embodiment, the iduronic acid-enriched polysaccharide synthesized from Formula III is represented by the structure of Formula II.

In another embodiment, the first step of the reaction comprises reacting a non-sulfated N-acetyl heparosan (HS) polysaccharide with sulfotransferase and epimerase, such that the heparosan polysaccharide is at a final concentration of 0.1 mM. In another embodiment, the heparosan polysaccharide is at a final concentration of 1 mM. In another embodiment, the heparosan polysaccharide is at a final concentration of 10 mM. In another embodiment, the heparosan polysaccharide is at a final concentration of 50 mM. In another embodiment, the heparosan polysaccharide is at a final concentration of 100 mM. In another embodiment, the heparosan polysaccharide is at a final concentration ranging from 0.1-1 mM. In another embodiment, the heparosan polysaccharide is at a final concentration ranging from 1-10 mM. In another embodiment, the heparosan polysaccharide is at a final concentration ranging from 10-50 mM. In another embodiment, the heparosan polysaccharide is at a final concentration ranging from 50-100 mM.

In another embodiment, the reaction of is conducted in a solution comprising 50 mM MES (pH 7.0), 1% (W/V) triton X-100, 5 mM MgCl2, 5 mM MnCl2, 2.5 mM CaCl2, 0.075 mg/ml protamine chloride, 1.5 mg/ml BSA or 25 mM HEPES, 40 mM CaCl2, pH 6.5, with or without the addition of p40. In another embodiment, alternative divalent cations are utilized, as is well known in the art. In another embodiment, reaction conditions are carried out at a pH ranging from 5.5-7.5. In another embodiment, O-sulfonization is performed at a temperature between 30 and 40° C. for a time comprised of between 1 and 24 hours.

In another embodiment, the synthesis is carried out in a range of 1-1,000 ml total volume. In one embodiment, the reaction is carried out at a 2500 µl total volume. According to this aspect of the invention, the following components were added: polysaccharide (final concentration was 1 mM equivalent of unmodified disaccharide), 1250 µl of 2× buffer, 50 ng of the expressed sulfotransferase or epimerase, [$^{35}$S] 3'-phosphoadenosine 5'-phosphosulfate (PAPS) (1.0×10$^7$ cpm) or [$^{32}$S] PAPS (final concentration of 20 µM), and the appropriate amount of water. It is to be understood that the amounts of the above components can be scaled up proportionately, as well, and as such represent additional embodiments of the invention.

The reaction mixture is, in one embodiment, incubated at 37° C. for 12 hours, then diluted to 5 ml with DEAE wash buffer and purified on DEAE column. In another embodiment, the reaction is stopped by heating the reaction mixture at 70° C. followed by centrifugation at 10,000 g for 3 minutes.

The products obtained via the synthesis method of the invention may be characterized by any number of methods well known to one skilled in the art. In one embodiment, the products are characterized via proton and carbon $^{13}$NMR analysis. In another embodiment, products may be analyzed by capillary HPLC-ESI-TOF-MS, via methods exemplified herein.

In another embodiment, products derived from the syntheses outlined herein may be analyzed via biological assays, which assess anti-Xa, aPTT, HCII, Anti-IIa activity, and affinity for ATIII.

In another embodiment, the compound comprising N-deacetylate N-sulfate derivatives of non-sulfated N-acetyl heparosan (HS) polysaccharide generated by the methods disclosed, comprise 3-O sulfated tetrasaccharides, which are resistant to cleavage by heparitinases, as was evident in Example 3, herein. In another embodiment, the compounds generated via the methods disclosed herein possess at least 4 times greater anti-coagulant activity than that of heparin, as measured by factor Xa assays. In another embodiment, the compounds generated via the methods disclosed herein possess diminished PF4 binding capacity as compared to heparin.

In another embodiment, the molecular weight of the products of the synthesis can be tailored at any stage by standard chemical or enzymatic cleavage techniques which have been utilized in similar fashion to produce low molecular weight heparin, thereby producing additional, low molecular weight anticoagulant compounds, with properties similar to that of the compound represented by the structure of Formula I.

In one embodiment, low molecular weight compounds of N-deacetylate N-sulfate derivatives of non-sulfated N-acetyl heparosan (HS) polysaccharide characterized by the structure of Formula I are generated via digestion of the unfractionated or partially fractionated product with heparatinase, thereby obtaining compounds of Formula I with a lower molecular mass.

In one embodiment, the invention provides lower molecular mass derivatives of non-sulfated N-acetyl heparosan polysaccharide obtained via methodology disclosed herein. In one embodiment, the lower molecular mass derivative is ?U-GlcNS3S6S, or in another embodiment, the derivative is ?U-GlcNAc6S-GlcA-GlcNS3S6S, or in another embodiment, the derivative is ? U-GlcNAc6S-GlcA-GlcNS3S, or in another embodiment, the derivative is ? U-GlcNS6S-GlcA-GlcNS3S6S, with structures of which are represented by the formulas below:

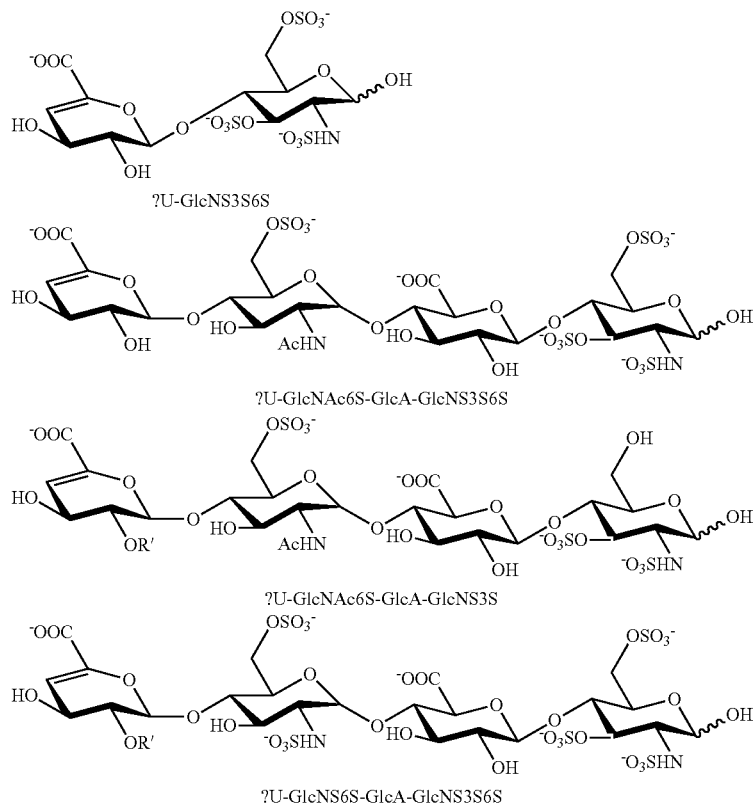

?U-GlcNS3S6S

?U-GlcNAc6S-GlcA-GlcNS3S6S

?U-GlcNAc6S-GlcA-GlcNS3S

?U-GlcNS6S-GlcA-GlcNS3S6S

In another embodiment, the invention provides compositions comprising lower molecular mass derivatives herein described.

The heparatinases used to generate low molecular weight compounds of Formula I as described, may be derived from any source, both native or recombinant (see for example, U.S. Pat. No. 5,290,695), representing additional embodiments of the invention. In one embodiment, Heparitinase I is utilized. In another embodiment, Heparitinase II is utilized. In another embodiment, Heparitinase III is utilized. In another embodiment, any heparanase or endoglucuronidase may be utilized to cleave the polymers, and any resulting oligosaccharide is to be considered as part of the present invention.

In one embodiment, when sufficient digestion of the unfractionated or partially fractionated compound of Formula I has taken place, the heparatinase is inactivated. Inactivation of the heparatinase can be effected in any one of a plurality of techniques employed in the art for enzyme inactivation, including, but not limited to, heat inactivation, dilution, e.g., by dialysis, exposure to extreme pH followed, for example, by neutralization, and the like. The time required for sufficient digestion of the unfractionated or partially fractionated compound of Formula I will depend on several factors, including, but not limited to, active heparatinase concentration, temperature, pH and solutes other than the enzyme and substrate. One ordinarily skilled in the art would know how to modify these factors so as to obtain controlled and repetitive performance.

It will be appreciated by one ordinarily skilled in the art that the heparatinase enzyme can be bound to a solid matrix and that the time of digestion of the unfractionated or partially fractionated heparin or heparan sulfate can thus by controlled by controlling the exposure time of the unfractionated or partially fractionated compound of Formula I to the solid matrix.

Monitoring the digestion reaction according to the present invention can be effected by periodic sampling and one of a plurality of known techniques, including, but not limited to, high performance liquid chromatography, conventional chromatography, mass spectroscopy, gel electrophoresis and the like. Thus, when sufficient digestion of the unfractionated or partially fractionated compound of Formula I has taken place as determined by any one of the above techniques the heparatinase is inactivated, so as to control the molecular mass of the resulting digestion products.

According to another embodiment of the present invention, the compound of Formula I with a relatively low molecular mass generated following sufficient digestion with heparatinase is precipitated, e.g., by the addition of ethanol and salt and appropriate centrifugation.

In another, the compound of Formula I with a relatively low molecular mass generated following sufficient digestion with heparatinase is size fractionated and low molecular weight compound of Formula I of a specific molecular mass range is collected. Size fractionation can be effected by any one of a variety of techniques known in the art, including, but not limited to, high performance liquid chromatography, conventional chromatography, mass spectroscopy, gel electrophoresis, differential filtration, differential centrifugation, differential dialysis and the like.

In one embodiment, the ATIII binding sites in the compound represented by the structure of Formula I are maintained, in compounds thus generated.

In another embodiment, there is provided a method for the preparation of novel glycosaminoglycans, comprising the steps of contacting a non-sulfated N-acetyl heparosan (HS) polysaccharide with the enzymes N-deacetylase-N-sulfotransferase and glucuronosyl C-5 epimerase to generate an iduronic acid-enriched polysaccharide; contacting the iduronic acid-enriched polysaccharide with the enzymes 6-O sulfotransferase (6-OST) and 3-O sulfotransferase (3-OST); and isolating the product, which yields N-deacetylate N-sulfate derivatives of non-sulfated N-acetyl heparosan.

It is to be understood that the method, according to this aspect of the invention, includes all embodiments herein described, for the generation of novel glycosaminoglycans.

In another embodiment, the invention provides a method for controlling coagulation in a subject. The method comprises providing the subject with an effective amount of a compound comprising N-deacetylate N-sulfate derivatives of non-sulfated N-acetyl heparosan (HS) polysaccharide, represented by the structure of Formula I. In another embodiment, the invention provides a method for controlling coagulation in a subject via providing the subject with a composition comprising N-deacetylate N-sulfate derivatives of non-sulfated N-acetyl heparosan (HS) polysaccharide, represented by the structure of Formula I In another embodiment, the invention provides a method for preventing or treating thrombosis in a subject, comprising providing the subject with an effective amount of a compound comprising N-deacetylate N-sulfate derivatives of non-sulfated N-acetyl heparosan (HS) polysaccharide, represented by the structure of Formula I.

As used herein, the terms "providing", or "contacting" and corresponding forms of the words, refer to both direct and indirect exposure to a compound or composition of the invention.

It is to be understood that the N-deacetylate N-sulfate derivatives of non-sulfated N-acetyl heparosan (HS) polysaccharide, represented by the structure of Formula I provided to the subject, may comprise any embodiment as herein described.

According to these aspects of the invention, the N-deacetylate N-sulfate derivatives of non-sulfated N-acetyl heparosan (HS) polysaccharide, represented by the structure of Formula I provided to the subject are in an amount sufficient to cure, or at least partially diminish the subject's need for such treatment or preventive measures.

In one embodiment, the subject suffers from a disease and the compound of Formula I or derivatives thereof are administered in an amount sufficient to cure or at least partially arrest the disease and/or its symptoms. In one embodiment, the disease is a blood coagulation disorder, e.g., a hemostatic or thrombotic abnormality, coagulation inhibitor deficiency, or a disseminated intravascular condition. In another embodiment, the disease is a result of a deficiency in at least one blood coagulation factor, e.g., Factor VIII, IX (or both) such as in hemophilia type a, b, or c (See e.g., Williams Hematology, infra, Table 126-1 in Chapter 126).

An amount adequate sufficient to cure or at least partially arrest the disease and/or its symptoms is defined as an "effective amount". Amounts effective for this use will depend upon the severity of the disease and the general state of the patient's health. Single or multiple administrations of the compositions may be administered depending on the dosage and frequency as required and tolerated by the subject. In any event, the composition should provide a sufficient quantity of the active agents of the formulations of this invention to effectively treat (ameliorate one or more symptoms) the subject.

In another embodiment, the N-deacetylate N-sulfate derivatives of non-sulfated N-acetyl heparosan (HS) polysaccharide represented by the structure of Formula I are administered to the subject as part of a composition. It is to be understood that compositions as such are to include all embodiments described herein.

Routes of administration of the compounds and compositions of the invention include, but are not limited to oral or local administration, such as by aerosol, intramuscularly, transdermally or transmurally. In another embodiment, the compounds and/or compositions are provided parenterally, such as intra-arterially (IA) or intravenously (TV). In another embodiment, the compounds and/or compositions are provided subcutaneously (SC).

The term "transmural" is intended to include provision of localized delivery of the composition into the blood vessel or body lumen wall including neointimal, intimal, medial, advential, and periviascular spaces, particularly adjacent to the target site.

In another embodiment, delivery of the compounds and/or compositions of the invention may be accomplished through a variety of known intravascular drug delivery systems. Such delivery systems include intravascular catheter delivery systems. A variety of catheter systems useful for the direct transmural infusion into the blood vessel are well known in the art For purposes of practicing the invention, any of a variety of diagnostic or therapeutic type catheters could be used.

In another embodiment, the compounds and/or compositions of this invention are provided to the subject in conjunction with an angioplasty, and balloon catheters can be used. Catheters having spaced-apart or helical balloons for expansion within the lumen of a blood vessel and delivery of a therapeutic agent to the resulting isolated treatment site are described in U.S. Pat. Nos. 5,279,546; 5,226,888; 5,181,911; 4,824,436; and 4,636,195. Non-balloon drug delivery catheters are described in U.S. Pat. Nos. 5,180,366; 5,112,305; and 5,021,044; and PCT Publication WO 92/11890. Catheters that provide for distal vessel access, as well as stents may also can be used, in another embodiment of this invention.

Compositions can be administered in a variety of unit dosage forms depending upon the method of administration. Suitable unit dosage forms, include, but are not limited to powders, tablets, pills, capsules, lozenges, suppositories, etc. Transdermal administration may be accomplished by application of a cream, rinse, gel, etc. capable of allowing the active compounds to penetrate the skin. Parenteral routes of administration may include, but are not limited to, electrical or direct injection such as direct injection into a central venous line, intravenous, intramuscular, intraperitoneal, intradermal, or subcutaneous injection.

Compositions of this invention suitable for parenteral administration include, but are not limited to, sterile isotonic solutions. Such solutions include, but are not limited to, saline and phosphate buffered saline for injection into a central venous line, intravenous, intramuscular, intraperitoneal, intradermal, or subcutaneous injection.

In one embodiment, the compounds of the present invention are combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s). The excipients are preferably sterile and generally free of undesirable matter. These compositions may be sterilized by conventional, well-known sterilization techniques.

The concentration of the derivatives in the formulation can vary widely, and will be selected, in one embodiment, based on fluid volumes, or in another embodiment, based on viscosities, or in another embodiment, based on body weight and the like in accordance with the particular mode of administration selected and the subject's need.

The following are meant to provide materials, methods, and examples for illustrative purposes as a means of practicing/executing the present invention, and are not intended to be limiting.

EXAMPLES

Materials and Methods

Reagents

HS precursor polysaccharide was prepared from *E. coli* K5 strain (9). Heparan Sulfate C-5 epimerase, 3-OST1, 6-OST2a, and NDST2 sulfotransferases were all cloned and expressed in baculovirus system (12, 13, 15, 16, 17). [$^{35}$S] PAPS and [$^{34}$S]-PAPS were prepared as reported earlier whereas [$^{32}$S]PAPS was purchased from Calbiochem. All chemicals were purchased from Sigma. ATIII and Factor Xa were from Haematologic Technologies Inc. Chromogenic substrate S-2765 was from Chromogenix. Heparitinase I, II and III were obtained from Seikagagu. APS kinase was a generous gift from Professor I. H. Segel (Univ. of California, Davis).

cDNA Cloning of Human Glucuronyl C5 Epimerase

A cDNA clone coding for human C5 epimerase was isolated from a human fetal brain cDNA panel (origene, Rockville, Md.) by screening with PCR primers spanning nucleotides 7-157 of the coding region. A donor plasmid for the preparation of recombinant baculovirus expressing a soluble form of the epimerase was constructed in pFastBac HT plasmid (Gibco, Grand Island, N.Y.) modified by the insertion of honeybee melittin signal peptide ahead of the histidine tag. The construction employed a synthetic oligonucleotide adapter that also encoded amino acids 35-44 of the epimerase and two restriction fragments isolated from the cDNA clone (TaqI to EcoRI and EcoRI to SacI) that incorporate the rest of the epimerase coding region.

Baculovirus Expression and Purification of Glucuronyl C5 Epimerase

Human glucuronyl C5 epimerase recombinant baculovirus was prepared using the donor and the Bac-to-Bac baculovirus expression system (Life Technologies, Inc. Grand Island, N.Y.) according to the manufacturer's protocol, except that recombinant bacmid DNA was purified using an endotoxin-free plasmid purification kit (Qiagen, Inc. Valencia, Calif.) and transfection of Sf9 cells was scaled up to employ 15 µg of bacmid DNA and $2.5 \times 10^7$ exponentially growing cells in four 100-mm dishes. Medium containing recombinant baculovirus was harvested at 3 days post-transfection and amplified twice for about 65 hours each on Sf9 cells. The resulting high-titer viral stock was stored in aliquots (0.75 ml) sufficient to infect $3.5 \times 10^8$ cells, as determined by Western blotting of medium from infected cells using (his)4 antibody (Qiagen). Infected cells were plated in ten 150 mm dishes and incubated at 26° C. for 90-96 hours. The pooled medium was centrifuged at 400×g, adjusted to 10 mM in HEPES, titrated to pH 7.4, chilled on ice for 30 minutes and centrifuged at 16,000×g. The clarified pool diluted in half with 10 mM HEPES, pH 7.4, made 1 mM in PMSF, and applied to an 8 ml column of ToyoPearl AF heparin 650M (TOSOHAAS, Montgomeryville, Pa.). The column was washed with 40 ml of HCG 50 (10 mM HEPES, pH 7.4, 2% glycerol, 0.6% CHAPS, 50 mM NaCl) and eluted with an 80 ml linear gradient of 50 to 600 mM NaCl in HCG. Aliquots of selected 1 ml fractions were analyzed by western blotting for the presence of the histidine tag, adjusted to 500 mM in NaCl, 10 mM in imidazole and concentrated an Amicon YM-10 membrane (Amicon, Bedford, Mass.) to about 3 ml.

Digestion of Polysaccharides with Heparitinase I, II, and III

Polysaccharides were digested with 1 mU of Hep I, II and III in a total volume of 100 µl of 40 mM Ammonium acetate containing 1 mM Calcium chloride buffer (pH 7.0) at 37° C. overnight.

Flow Injection Capillary Liquid Chromatography

An Ultimate capillary HPLC workstation (Dionex, Sunnyvale, USA) was used for microseparation. UltiChrom software was used in data acquisition and analysis. A gradient elution was performed, using a binary solvent system composed of water (eluent A) and 70% aqueous methanol (eluent B), both containing 8 mM acetic acid and 5 mM dibutylamine as an ion-pairing agent. HPLC separations were performed on a 0.3 mm×250 mm C18 polymeric silica column (Vydac, Hesperia, USA). The column temperature was maintained at 25° C. and the flow rate was set to 5 mL min-1. Sample volumes of 6.3 mL were injected. The chromatographic conditions were optimized for resolution of disaccharides. In brief, non-sulfated disaccharide was eluted with 100% A, single sulfated disaccharides were eluted with 10% B, isocratic elution with 20% B for double sulfated disaccharides, followed by isocratic elation with 35% B for triple sulfated disaccharide. The column was washed and equilibrated by further elution with 100% B for 10 min, returning to 100% A for 10 min at the end of the run. The absorbance of the column eluate was monitored at 232 nm.

Mass Spectrometry

Mass spectra were acquired on a Mariner BioSpectrometry Workstation ESI time-of-flight mass spectrometer (PerSeptive Biosystems, Framingham, Mass.). In the negative-ion mode, the instrument was calibrated with bis-trifluoromethyl benzoic acid, heptadecafluorononanoic acid, and perfluorotetradecanoic acid. Nitrogen was used as a desolvation gas as well as a nebulizer. Conditions for ESI-MS were as follows: nebulizer flow 0.75 L/min, nozzle temperature 140° C., drying gas (N2) flow 1.2 L/min, spray tip potential 2.8 kV, nozzle potential 70 V, and skimmer potential 12 V. Negative ion spectra were generated by scanning the range of m/z 40-2000. During analyses, the indicated vacuum was $1.9 \times 10^{-6}$ Torr.

Enzymatic Modification with Recombinant Enzymes: NDST2, C5 Epi 6OST2a, and 3-OST1

The labeling 2× buffer contains 50 mM MES, (pH 7.0), 1% (W/V) triton X-100, 5 mM $MgCl_2$, 5 mM $MnCl_2$, 2.5 MM $CaCl_2$, 0.075 mg/ml protamine chloride, 1.5 mg/ml BSA or 25 mM HEPES, 40 mM $CaCl_2$, pH 6.5 with or without p40. For a 2500 μl reaction, the following were assembled: polysaccharide (final concentration was 1 mM equivalent of unmodified disaccharide), 1250 μl of 2× buffer, 50 ng of the expressed sulfotransferase or epimerase, [$^{35}$S] 3'-phosphoadenosine 5'-phosphosulfate (PAPS) ($1.0 \times 10^7$ cpm) or [$^{32}$S] PAPS (final concentration of 20 μM), and the appropriate amount of water. The reaction was incubated at 37° C. for 12 hours, then diluted to 5 ml with DEAE wash buffer and purified on DEAE column. Alternatively, the reaction was stopped by heating at 70° C. and the reaction mixture was centrifuged at 10,000 g for 3 min and the supernatant was used for gel mobility shift analysis. Modified polysaccharide was digested with heparitinases I, II and III and was analyzed by capillary HPLC-ESI-TOF-MS.

Gel Mobility Shift Assay

Heparin-ATIII binding buffer contained 12% glycerol, 20 mM Tris-HCl (pH 7.9), 100 mM KCl, 1 mM EDTA, and 1 mM DTT. For a typical 20 μl binding reaction, radiolabeled polysaccharide (10,000 cpm) was mixed with AT-III (1 μg) in the binding buffer. The reaction mixture was incubated at room temperature (23° C.) for 20 min and was then applied to a 4.5% native polyacrylamide gel (with 0.1% of bis-acrylamide). The gel buffer was 10 mM Tris (pH 7.4) and 1 mM EDTA, and the electrophoresis buffer was 40 mM Tris (pH 8.0), 40 mM acetic acid, 1 mM EDTA. The gel was run at 6 volts/cm for 1-2 hours with an SE 250 Mighty Small II gel apparatus (Hoefer Scientific Instruments, San Francisco). After electrophoresis, the gel was transferred to 3 MM paper and dried under vacuum. The dried gel was autoradiographed by a PhosphorImager 445SI (Molecular Dynamics, Sunnyvale, Calif.). The image was analyzed with NIH Image 1.60 and band intensities were evaluated.

Factor Xa Assay

Human factor Xa (10.4 mg/ml 50% glycerol, 820 units/mg) (Hematologic Technologies, Essex Junction, Vt.) was used for assay. Factor Xa was diluted 1:200 with PBS containing 1 mg of bovine serum albumin (4 units/ml and 15 units/ml, respectively). ATIII (2.5 mg/ml) (GlycoMed, Calif.) was diluted 1:200 to give a $2 \times 10^7$ M stock solution. The chromogenic substrate S-2765 was from Chromogenix (West Chester, Ohio) and the stock solution of 1 mM with 1 mg/ml Polybrene in water was prepared. Heparin (174 international units/mg, Sigma) was used as a standard. The N-deacetylated N-sulfated polysaccharide product was used for factor Xa studies (10 ng). The protocol involved adding 25 μl of ATIII ($2 \times 10^7$ M) to 25 μl of a serial dilution of heparin standards or N-deacetylated N-sulfated polysaccharide in Tris-EDTA (50 mM Tris, 7.5 mM EDTA, and 175 mM NaCl (pH 8.4)) buffer. The reaction was incubated at 37° C. for 75 seconds. Factor Xa (25 μl, 4 units/ml) was added. After incubating at 37° C. for 195 seconds, 25 μl of S-2765 was added. The absorbance at 405 nm was read every minute for 10 minutes using a Beckman UV spectrometer.

Example 1

Effective Coupling of Enzyme Activities for Synthesis of an N-Sulfated N-Deacetylated Polysaccharide A non-sulfated N-acetyl heparosan (HS) polysaccharide, the compound represented by the structure of Formula III (FIG. 1, step 1) was isolated from the *E. coli* strain K5 (9), which resembles the unmodified nascent HS chain, and was used as a starting material. Synthesis of an N-sulfated polysaccharide enriched with iduronic acid (represented by the structure of Formula II) was catalyzed by N-deacetylase-N-sulfotransferase (NDST) and C-5 epimerase (step 2). These two initial modifications were the essential gateway for subsequent enzymatic modifications (10).

A single protein catalyzes both N-deacetylation and N-sulfation. These two reactions are tightly coupled in vivo, since free glucosamine residues are rarely found in HS and Heparin, even though each activity can be studied separately in vitro. The NDST enzyme exists as four isoforms in humans (11). The NDST2 isoform was utilized to selectively N-deacetylate and N-sulfate glucosamine units (12). The deacetylation and N-sulfation was carried out in the presence of the Heparan Sulfate C-5 epimerase (13, 14) enzyme, in order to generate the iduronic acid-enriched polysaccharide (the compound represented by the structure of Formula II).

The stereochemical nature at the C-5 carbon of uronic acid is reversed during transformation of the compound represented by the structure of Formula II to the compound represented by the structure of Formula II of FIG. 1. Epimerization proceeds on condition that uronic acid residues are located at the reducing side of N-sulfated glucosamine residues. Epimerization will not proceed should the uronic acid be O-sulfated or be adjacent to O-sulfated glucosamine residues or N-acetylglucosamine units (10, 14). The stereochemical constraint imposed indicates that epimerization occurs immediately following N-deacetylation and N-sulfation but prior to O-sulfation.

The sterochemical constraint was exploited in the synthetic strategy of the present invention. NDST2 and C5 epimerase activity was coupled in order to prepare in a single step N-sulfated polysaccharide (the compound represented by the structure of Formula II) containing both glucuronic and iduronic acid, without 2-O sulfation.

The final step (step 3) in the synthesis of the N-deacetylate N-sulfate derivatives of non-sulfated N-acetyl heparosan (HS) polysaccharides (the compound represented by the structure of Formula I) was catalyzed by combined activity of 6-O sulfotransferase (6-OST) and 3-O sulfotransferase (3-OST). There are three heparan sulfate 6-O sulfotransferase isoforms: 6-OST1, 6-OST2 (6-OST2a and 6-OST2b are two splice variants) and 6-OST3 (15). Though all three isoforms sulfate CDSNS-Heparin equally well (15), N-sulfo-heparosan was preferentially sulfated in the following order: 6-OST2 sulfated to a greater extent than 6-OST3, which sulfated to a much greater extent as compared to 6-OST1. The 6-OST2a isoform was utilized to catalyze the 6-O sulfation of glucosamine units in Formula II.

6-O sulfation was coupled with 3-O sulfation, which is catalyzed by 3-OST1 sulfotransferase (16). There are as many as five isoforms of heparan sulfate 3-O sulfotransferases, namely 3-OST1, 3-OST2, 3-OST3, 3-OST4, and 3-OST5 (17, 18). 3-OST1 has been shown primarily responsible for generating the anticoagulant heparan (19). 3-OST1 generally acts on glucosamine units flanked by the reducing side of glucuronic acid (GlcUA) and the non-reducing side of iduronic acid (IdoA) to generate anti-thrombin (AT) III antibody binding structures containing GlcUA-GlcNS₃S and GlcUA-GlcNS₃S₆S (19-21). Coupling of 6-O sulfation and 3-O sulfation was conducted in order to determine whether this coupling would shorten the time required for total synthesis of the compound represented by the structure of Formula I, which was readily accomplished.

Example 2

N-Deacetylate N-Sulfate Derivatives of Non-Sulfated N-Acetyl Heparosan (HS) Polysaccharide Anti-Coagulant Activity The final step was also carried out in the presence of radioactive PAP$^{35}$S to prepare the radiolabeled compound represented by the structure of Formula I, in order to test its ability to bind to anti-thrombin III (ATIII) by gel mobility shift assay (22). The synthesized compound represented by the structure of Formula I was found to bind to ATIII. In the presence of ATIII, the compound bound specifically to ATIII and hence its mobility was retarded, whereas in the absence of ATIII, the compound migrated more rapidly [FIG. 2].

A greater percentage of the compound of Formula I bound ATIII as compared to in vitro modified commercial heparin. This result was further confirmed by a heparin-dependent factor Xa inhibition assay [FIG. 3]. The specific activity of the compound of Formula I was approximately 4-5 times that of commercial-heparin.

Example 3

N-Deacetylate N-Sulfate Derivatives of Non-Sulfated N-Acetyl Heparosan (HS) Polysaccharide Consists of Multiple ATIII Binding Sites Finally, the compound of Formula I was subjected to structural analysis following cleavage by heparitinases I, II and III, via capillary liquid chromatography coupled to electro-spray mass spectrometry (LC/MS) (23) [FIG. 4]. The LC/MS analysis showed one major tri-sulfated disaccharide containing a 3-O sulfated glucosamine unit, ? U-GlcNS3S6S, corresponding to molecular ion 576.0 [M-1H]-1 and two other minor disaccharides, ? U-GlcNS3S and ? U-GlcNS6S, corresponding to molecular ion 496.1 [M-1H]-1. The LC/MS analysis also confirmed the presence of many tetrasaccharides, which are resistant to further cleavage by heparitinases, due to the presence of 3-O sulfate groups. These 3-O sulfated tetrasaccharides are: ? U-GlcNAc6S-GlcA-GlcNS3S6S with molecular ion 517.0 [M-2H]-2; ? U-GlcNAc6S-GlcA-GlcNS3S with molecular ion 477.1 [M-2H]-2; ? U-GlcNS6S-GlcA-GlcNS3S6S with molecular ion 536.0 [M-2H]-2.

This result demonstrated that the compound of Formula I consists of multiple ATIII binding sites within the polymer and indicates why the compound has greater ability to inhibit factor Xa. Since the compound is free of 2-O sulfated iduronic acid residues, we expect that it will have a reduced ability to bind to PF4 which should decrease its ability to cause HIT and at the same time increase its anticoagulant activity against the platelet-rich thrombi present on the arterial side of the circulation.

REFERENCES (OTHER REFERENCES INCLUDED IN TEXT)

1. J. McLean, Am. J. Physiol. 41, 250 (1916).
2. I. Capila, R. J. Linhardt, Angewandte Chemie-International Edition 41, 391-412 (2002).
3. P. S. Damus, M. Hicks, Rosenber. Rd, Nature 246, 355-357 (1973).
4. R. D. Rosenberg, P. S. Damus, J Biol Chem 248, 6490-505 (Sep. 25, 1973).
5. P. Sinay et al., Carbohydrate Research 132, C5-C9 (1984).
6. M. Petitou et al., Nature 398, 417-422 (Apr. 1, 1999).
7. B. H. Chong, 1. Fawaz, C. N. Chesterman, M. C. Berndt, Br J Haematol 73, 235-40 (October 1989).
8. S. E. Stringer, J. T. Gallagher, J Biol Chem 272, 20508-14 (Aug. 15, 1997).
9. W. F. Vann, M. A. Schmidt, B. Jann, K. Jann, Eur J Biochem 116, 359-64 (May 15, 1981).
10. R. D. Rosenberg, N. W. Shworak, J. Liu, J. J. Schwartz, L. J. Zhang, Journal of Clinical Investigation 99, 2062-2070 (May 1, 1997).
11. J. Aikawa, K. Grobe, M. Tsujimoto, J. D. Esko, J Biol Chem 276, 5876-82 (Feb. 23, 2001).
12. A. Orellana, C. B. Hirschberg, Z. Wei, S. J. Swiedler, M. Ishihara, J Biol Chem 269, 2270-6 (Jan. 21, 1994).
13. J. Li et al., J Biol Chem 272, 28158-63 (Oct. 31, 1997).
14. P. Campbell et al., J Biol Chem 269, 26953-8 (Oct. 28, 1994).
15. H. Habuchi et al., J Biol Chem 275, 2859-68 (Jan. 28, 2000).
16. J. Liu, N. W. Shworak, L. M. S. Fritze, J. M. Edelberg, R. D. Rosenberg, Journal of Biological Chemistry 271, 27072-27082 (Oct. 25, 1996).
17. N. W. Shworak et al., Journal of Biological Chemistry 274, 5170-5184 (Feb. 19, 1999).
18. G. Xia et al., J Biol Chem 277, 37912-9 (Oct. 4, 2002).
19. J. A. Liu et al., Journal of Biological Chemistry 274, 5185-5192 (Feb. 19, 1999).
20. N. Razi, U. Lindahl, J Biol Chem 270, 11267-75 (May 12, 1995).
21. L. Zhang et al., J Biol Chem 276, 28806-13 (Aug. 3, 2001).
22. Z. L. Wu, L. Zhang, D. L. Beeler, B. Kuberan, R. D. Rosenberg, Faseb J 16, 539-45 (April 2002).
23. B. Kuberan et al., Journal of the American Chemical Society 124, 8707-8718 (Jul. 24, 2002).
24. K. J. Bame, Glycobiology 11, 91R-98R (June 2001).

What is claimed is:

1. A compound comprising the structure of Formula I:

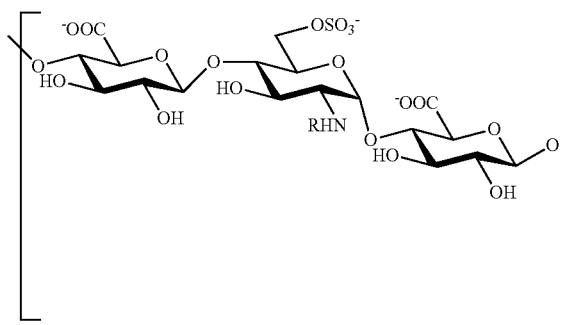

-continued

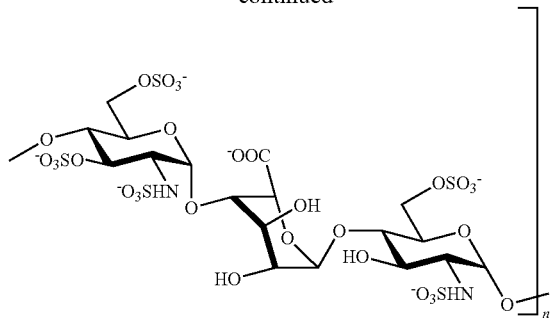

wherein
R is SO$_3^-$ or COCH$_3$; and
n is an integer 100-100,000; and salts thereof,
in which the compound is free of 2-O sulfated iduronic acid residues, wherein the compound possesses at least 4 times greater anti-coagulant activity than that of heparin as measured by factor Xa assays.

2. The compound according to claim 1, wherein R is SO$_3^-$.

3. The compound according to claim 1, wherein R is COCH$_3$.

4. The compound according to claim 1, wherein the compound comprises at least one 3-O sulfated tetrasaccharides of ΔU-GlcNAc6S-GlcA-GlcNS3S6S or ΔU-GlcNS6S-GlcA-GlcNS3S6S.

5. A composition comprising the compound of claim 1.

6. A method for controlling coagulation in a subject, comprising administering to said subject an effective amount of the compound of claim 1.

7. A method for preventing or treating thrombosis in a subject, comprising administering to said subject an effective amount of the compound of claim 1, effective to inhibit coagulation, thereby preventing or treating thrombosis.

* * * * *